United States Patent [19]

Ryals et al.

[11] Patent Number: 5,348,743
[45] Date of Patent: Sep. 20, 1994

[54] ANTI-PATHOGENICALLY EFFECTIVE COMPOSITIONS COMPRISING LYTIC PEPTIDES AND HYDROLYTIC ENZYMES

[75] Inventors: John A. Ryals, Durham, N.C.; Philippe B. Gay, Mulhouse, France; Patricia A. Ahl-Goy, Basel, Switzerland

[73] Assignee: Ciba-Geigy Corporation, Ardsley, N.Y.

[21] Appl. No.: 82,310

[22] Filed: Jun. 25, 1993

Related U.S. Application Data

[63] Continuation of Ser. No. 491,801, Mar. 12, 1990, abandoned.

[51] Int. Cl.$^5$ ............................................. A61K 37/54
[52] U.S. Cl. ....................................... 424/94.61; 514/2; 514/21; 530/324
[58] Field of Search ............... 424/94.61; 514/2, 21; 530/324

[56] References Cited

U.S. PATENT DOCUMENTS 4,810,777  3/1989  Zasloff ............................... 530/326

FOREIGN PATENT DOCUMENTS

WO86/04356  7/1986  PCT Int'l Appl.
WO88/00976  2/1988  PCT Int'l Appl.
WO88/05826  8/1988  PCT Int'l Appl.
WO89/04371  3/1989  PCT Int'l Appl.
WO89/11291  11/1989  PCT Int'l Appl.
8900048  1/1989  World Int. Prop. O.

OTHER PUBLICATIONS

Kauffmann et al., *EMBO J.*, 6:3209–3212 (1987).
Selsted et al., *Infection and Immunity*, 55:2281–2286 (1987).
Legrand et al., *PNAS (USA)*, 84:6750–6754 (1987).
Terry et al., *J. Biolog. Chem.*, 263:5745–5751 (1988).
Lehrer et al., *Infection and Immunity*, 52:902–904 (1986).
Ogasawara et al., *Chem. Abstracts*, 79:13362v (1973).
Bohlmann et al., *EMBO J.*, 7:1559–1565 (1988).
Schlumbaum et al., *Nature*, 324:365–367 (1986).
Mauch et al., *Plant Phys.*, 88:936–942 (1988).
Boller et al., *Planta*, 157:22–31 (1983).

*Primary Examiner*—Douglas W. Robinson
*Assistant Examiner*—Jean C. Witz
*Attorney, Agent, or Firm*—W. Murray Spruill; James Scott Elmer

[57] ABSTRACT

Anti-pathogenically effective compositions are provided containing a combination of hydrolytic enzymes and lytic peptides as the active agent. Methods of controlling the growth of pathogens using the anti-pathogenically effective compositions are provided. Transgenic plants that contain genes that are able to express lytic peptides and hydrolytic enzymes are also provided.

12 Claims, No Drawings

ANTI-PATHOGENICALLY EFFECTIVE COMPOSITIONS COMPRISING LYTIC PEPTIDES AND HYDROLYTIC ENZYMES

This application is a continuation of application Ser. No. 07/491,801, filed Mar. 12, 1990, abandoned.

FIELD OF THE INVENTION

The present invention relates to compositions for controlling plant pathogens by employing as active ingredients a combination of lytic peptides and hydrolytic enzymes. More particularly, this invention relates to anti-pathogenic compositions in which small amounts of chitinase and/or beta-1,3-glucanase are used to increase the effectiveness of lytic peptides by facilitating access of the lytic peptide(s) to the cell membrane of the pathogen. The present invention further relates to transgenic plants that are able to produce lytic peptides and hydrolytic enzymes as well as to methods for controlling said plant pathogens.

BACKGROUND OF THE INVENTION

It is known that some lytic peptides are active against a broad range of organisms while others produce little or no effect. It is also known that one target of the lytic peptides the membrane, The amino acid sequence of several lytic peptides with antimicrobial activity are disclosed in Jaynes et al., PCT Patent Application No. US88/03908.

Hydrolytic enzymes, such as chitinase and beta-1,3-glucanase, are known to inhibit fungal growth. Schlumbaum et al., *Nature*, 324:365-367 (1986); Mauch et al., *Plant Phys.*, 88:936-942 (1988); and Burri, *Diplomarbeit* (1989). It is also well known that chitinase and beta-1,3-glucanase are strongly induced in beans by ethylene treatment. Furthermore, those enzymes can be purified quite easily. Boller et al., *Planta*, 157:22-31 (1983).

Lehrer et al., *Infection and Immunity*, 52:902-904 (1986) disclose six antimicrobial peptides (AMPs) from rabbit granulocytes that are structurally homologous to human neutrophil defensins. Three of the rabbit AMPs (NP-1, NP-2 and NP-3a) are disclosed to be effective against *Candida albicans*. Lehrer et al. further disclose that NP-5, although not directly fungicidal against *C. albicans*, demonstrated what is termed a synergistic effect, an increase in the fungicidal activity of NP-1, when the fungus was exposed to both NP-5 and NP-1.

Ogasawara et al., *Chem. Abstracts*, 79: 13362v (1973) disclose that the combination of beta-1,3-glucanase and chitinase is an effective fungicide and bactericide useful in the treatment of rice.

Jaynes et al., PCT International Application No. PCT/US87/01710 discloses the inhibition of crop damage from *lepidoptera* larvae by expressing genes which code for chitinase enzyme in the target crop.

SUMMARY OF THE INVENTION

It is one object of the present invention to provide novel compositions for controlling plant pathogens (preferably fungi, bacteria and nematodes). These novel compositions demonstrate excellent activity against a broad range of pathogens affecting plants.

It is another object of the present invention to provide compositions in which the pathogen's membrane is more easily degraded by lytic peptides.

It is another object of the present invention to provide anti-pathogenically effective agents in which the anti-pathogenically effective activity is inducible.

It is another object of the present invention to provide anti-pathogenically effective compositions employing the above novel combinations of anti-pathogenic agents.

It is a further object of the present invention to provide transgenic plants with anti-pathogenic effective activity.

It is another object of the present invention to provide transgenic plants that contain DNA sequences coding for lytic peptides and hydrolytic enzymes.

It is one feature of the present invention that pathogens are exposed to hydrolytic enzymes which degrade the cell wall and make the pathogen's membrane more accessible to lytic peptides.

It is another feature of the present invention that inducible hydrolytic enzymes, chitinase and beta-1,3-glucanase, are used in combination with lytic peptides.

It is another feature of the present invention that the combination of hydrolytic enzymes is effective with a broad range of lytic peptides.

It is one advantage of the present invention that very small amounts of chitinase and beta-1,3-glucanase activity are effective to significantly increase the inhibitory effects of lytic peptides.

According to the present invention, anti-pathogenically effective compositions are provided employing as the active ingredient combinations of lytic peptides and hydrolytic enzymes. Lytic peptides attack the pathogen's cell membrane. Because the pathogen's cell membrane is protected by the cell wall, applicants proposed that the use of cell wall lytic enzymes might allow lytic peptides better access to the pathogen's cell membrane. The applicants further hypothesized that a combination of cell wall lytic enzymes with cell membrane lytic peptides would increase the inhibitory effect of the lytic peptides on pathogens. Applicants have found that only very small amounts of hydrolytic enzymes are necessary to significantly increase the inhibitory effect of all lytic peptides tested.

The term "active ingredient" is used to refer to the combination of one or more lytic peptides and one or more hydrolytic enzymes, which combination functions to inhibit growth of pathogens. The active ingredients of the present invention may be used as one component in anti-pathogenically effective compositions, formulations or preparations.

The term "agriculturally acceptable carriers" is used to refer to those substances, or combinations of substances, that are known in the art of agricultural compositions, and may include, where appropriate, solid or liquid adjuvants, solvents, as well as surfactants.

As used in the present application, a "pathogenically effective amount" of a substance or composition means an amount which will kill or inhibit the growth of the target plant pathogen when applied to a plant, or when expressed in a transgenic plant.

The term "plant pathogen" includes fungi, bacteria, nematodes and insects. The preferred target pathogens according to the present invention are fungi and bacteria.

The terms "lytic peptide" and "cell membrane lytic peptides" are used to refer to any peptide which is capable of anti-pathogenically effective activity due to its ability to penetrate, lyse or otherwise impair the pathogen's cell membrane. Some examples of lytic peptides that may be used in the present invention include the mammalian defensins, cecropins, thionins, mellitins, insect defensins, magainins, attacins, dipteris, sapecins, cacrutins, xenopsins, or hybrids thereof. For examples of the amino acid sequences of such lytic peptides, see Wilde et al., PCT Patent Application PCT/US89/02317; Lai et al., PCT Patent Application Nos. PCT/US86/00131 and PCT/US88/00324; Zasloff, U.S. Pat. No. 4,810,777; and Jaynes et al., PCT Patent Application No. PCT/US88/03908; Bohlmann et al., *EMBO*, 7: 1559-1565 (1988); Selsted et al., *Infection and Immunity*, 55: 2281-2286 (1987).

Also useful as the lytic peptides of the present invention are synthetic peptides, which may be derivatives of one of the lytic peptides above or hybrids thereof. One example of such a synthetic peptide is Synthetic Peptide No. 3, which is a derivative of a magainin and has the following amino acid sequence:

GIGKFLHSAK KFGKAFVGI MNS

See Terry et al., *J. Biol. Chem.*, 263: 5745-5751 (1988).

As used in the present application, the term lytic peptides also includes substances which are active against cell membranes, such as lysozymes and phospholipases. Unlike the above lytic peptides, the lysozymes of the present invention are able to penetrate, lyse or otherwise impair the pathogen's cell membrane through an enzymatic mechanism. The phospholipases attack the phospholipids of the cell membrane.

In place of lytic peptides, other cell-membrane-degrading components may be employed in the active ingredient of the present invention. For example, it is within the scope of the present invention to employ cell-membrane-degrading detergents such as Triton and SDS.

The terms "hydrolytic enzyme", "cell wall hydrolase," "plant hydrolase" and "cell wall hydrolytic enzyme" are used to refer to any enzyme that is able to assist in degradation of the cell wall of a pathogen. The hydrolytic enzyme may be applied exogenously, or may be constitutively, temporally or inducibly expressed in the cell. Examples of hydrolytic enzymes that may be used in the present invention include chitinase and beta-1,3-glucanase.

As used in the present application, the term "constitutive" refers to a hydrolytic enzyme or other substance that is present at all times in a plant cell. The term "inducible" refers to a hydrolytic enzyme or other substance that is present in the plant cell only when the plant is subjected to some stress, condition or external stimulus and the production or presence of the hydrolytic enzyme or other substance is thereby activated or increased.

Plant pathogens which may be the targets of the pesticidal compositions of the present invention include members of the following classes: bacteria (for example Pseudomonas, Xanthomonas and Erwinia); fungi, such as *Fungi imperfecti* (for example, Botrytis, Septoria); Ascomycetes (for example, Erysiphe, Monilinia); Oomcetes (for example, Peronospora, Phytophthora, Plasmopara and Pythium); Basidiomycetes (for example, Rhizoctonia and Puccinia); as well as to Colletotrichum; insects and nematodes (for example species of Meloidogyne, Caenorhabditis, Globora, Heterodera and Pratylenchus). For example, the fungal pathogens may include the species *Botrytis cinerea; Colletotrichum lagenarium; Erysiphe graminis,* a wheat pathogen; *Monilinia fructicola; Peronospora tabacina; Phytophthora parasitica; Plasmopara viticola; Pythium ultimum,* a soil pathogen; *Rhizoctonia solani,* another soil pathogen; and *Septoria nodorum,* a wheat pathogen.

Target crops to be protected within the scope of the present invention include the following species of plants: maize, cereals (e.g., wheat, barley, rye, oats, rice, sorghum and related crops), beet (e.g., sugar beet and fodder beet), drupes, pomes and soft fruit (e.g., apples, pears, plums, peaches, almonds, cherries, strawberries, raspberries and blackberries ), leguminous plants (e.g., beans, lentils, peas, soybeans), oil plants (e.g., rape, mustard, poppy, olives, sunflowers, coconuts, caster oil plants, cocoa beans, groundnuts), cucumber plants (e.g., cucumber, marrows, melons) fibre plants (e.g., cotton, flax, hemp, jute), citrus fruit (e.g., oranges, lemons, grapefruit, mandarins), vegetables (e.g., spinach, lettuce, asparagus, cabbages, carrots, onions, tomatoes, potatoes, paprika), lauraceae (e.g., avocados, cinnamon, camphor), or plants such as tobacco, nuts, coffee, sugar cane, tea, vines, hops, bananas and natural rubber plants, as well as ornamentals (composites).

The relative concentrations of the hydrolytic enzymes in the active ingredient of the present invention is defined in terms of units of activity. The standard unit of concentration ("standard concentration" or "c") of hydrolytic enzyme is defined as the concentration of that enzyme that will produce an absolute activity value equal to that found for the purified hydrolytic enzyme. For example, the standard unit of concentration for chitinase is defined as the concentration of chitinase which will produce an absolute activity of 88.86 nkatal/ml extract. The standard unit of concentration of beta-1,3-glucanase is defined as that concentration which demonstrates an absolute activity value equal to that found for the partially purified enzyme, e.g., 76.00 nkatal/ml extract.

DETAILED DESCRIPTION OF THE INVENTION

The present invention relates to anti-pathogenically effective compositions comprising combinations of lytic peptides with cell wall hydrolytic enzymes, such as chitinase and beta-1,3-glucanase. In a preferred embodiment of the present invention, both chitinase and beta-1,3-glucanase are present in the active ingredient in small amounts, for example, in relative concentrations of about 1/10 of the standard concentration (c) , or, more preferably, about 1/100 c. The hydrolytic enzymes most likely allow for greater accessibility to the pathogen's cell membrane for lytic peptides.

In a preferred embodiment, the lytic peptides of the present invention are present in the active ingredient in a concentration from about 0.1 ppm to about 1000 ppm, preferably from about 0.5 ppm to about 500 ppm, especially from about 1 ppm to about 200 ppm.

The concentrations of chitinase and beta-1,3-glucanase that were found to be active against the test pathogens, when applied in combination with lytic peptides, are present in many plant species, even without a previous stimulus that leads to an induction of these hydrolytic enzymes. However, the naturally present chitinases and glucanases are not pathogenesis-related, and are found in the vacuole rather than in the extracellular space of the plant cell. Boller et al., *Planta,* 157:22-31 (1983); Burri (1989). Thus, in one preferred embodiment of the present invention, the lytic peptide is used in combination with activated hydrolytic enzymes that are already present in a plant. Chitinase and beta-1,3-glucanase are both inducible in plants. Thus, in another preferred embodiment of the present invention, the production of chitinase and beta-1,3-glucanase is induced using an external stimulus.

Induction may be by chemical means, for example, chemicals known to act as inducers of pathogen related proteins in plants include ethylene, benzoic acid, salicylic acid, polyacrylic acid and substituted derivatives thereof. Induction may also be by other physiological and physical means, such as by high or low temperatures, physical wounding or by any other known inductive means.

The present invention further embraces the preparation of anti-pathogenically effective compositions in which the active ingredient is a combination of lytic peptides and hydrolytic enzymes. The active ingredient is homogeneously mixed with one or more compounds or groups of compounds described herein. The present invention also relates to methods of treating plants, which comprise application of the active ingredient, or anti-pathogenically effective compositions containing the active ingredient, to plants.

The active ingredients of the present invention are normally applied in the form of compositions together with one or more agriculturally acceptable carriers, and can be applied to the crop area or plant to be treated, simultaneously or in succession, with further compounds. These compounds can be both fertilizers or micronutrient donors or other preparations that influence plant growth. They can also be selective herbicides, insecticides, fungicides, bactericides, nematicides, mollusicides or mixtures of several of these preparations, if desired together with further carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers.

A preferred method of applying active ingredients of the present invention or an agrochemical composition which contains at least one of the active ingredients is leaf application. The number of applications and the rate of application depend on the intensity of infestation by the corresponding pathogen. However, the active ingredients can also penetrate the plant through the roots via the soil (systemic action) by impregnating the locus of the plant with a liquid composition, or by applying the compounds in solid form to the soil, e.g. in granular form (soil application). The active ingredients may also be applied to seeds (coating) by impregnating the seeds either with a liquid formulation containing active ingredients, or coating them with a solid formulation. In special cases, further types of application are also possible, for example, selective treatment of the plant stems or buds.

In order for the anti-pathogenically effective compositions to inhibit growth of a pathogen such as the fungus *S. nodorum*, it is assumed that the pathogen first comes into contact with the hydrolytic enzymes. After contact with chitinase and beta-1,3-glucanase, the fungal membrane is more accessible to lytic peptides. Additionally, it is important to note that a plant's response in defense of pathogenic infection consists of many different mechanisms. While the combinations of chitinase, beta-1,3-glucanase and various lytic peptides show a considerable inhibition of pathogenic growth by destroying the pathogen's cell wall and the pathogen's membrane, they most likely assist a plant's anti-pathogenic ability by providing access to other anti-pathogenic substances which are produced during a plant's hypersensitive response. Thus, the combinations of chitinase, beta-1,3-glucanase and lytic peptides of the present invention are effective agents for the control of pathogens.

The active ingredients are used in unmodified form or, preferably, together with the adjuvants conventionally employed in the art of formulation, and are therefore formulated in known manner to emulsifiable concentrates, coatable pastes, directly sprayable or dilutable solutions, dilute emulsions, wettable powders, soluble powders, dusts, granulates, and also encapsulations, for example, in polymer substances. Like the nature of the compositions, the methods of application, such as spraying, atomizing, dusting, scattering or pouring, are chosen in accordance with the intended objectives and the prevailing circumstances. Advantageous rates of application are normally from 50 g to 5 kg of active ingredient (a.i.) per hectare ("ha", approximately 2.471 acres), preferably from 100 g to 2 kg a.i./ha, most preferably from 200 g to 500 g a.i./ha.

The formulations, compositions or preparations containing the active ingredients and, where appropriate, a solid or liquid adjuvant, are prepared in known manner, for example by homogeneously mixing and/or grinding the active ingredients with extenders, for example solvents, solid carriers and, where appropriate, surface-active compounds (surfactants).

Suitable solvents include aromatic hydrocarbons, preferably the fractions having 8 to 12 carbon atoms, for example, xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol monomethyl or monoethyl ether, ketones such as cyclohexanone, strongly polar solvents such as N-methyl-2-pyrrolidone, dimethyl sulfoxide or dimethyl formamide, as well as epoxidized vegetable oils such as epoxidized coconut oil or soybean oil; or water.

The solid carriers used e.g. for dusts and dispersible powders, are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable nonsorbent carriers are materials such as calcite or sand. In addition, a great number of pregranulated materials of inorganic or organic nature can be used, e.g. especially dolomite or pulverized plant residues.

Depending on the nature of the active ingredient to be used in the formulation, suitable surface-active compounds are nonionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are the alkali metal salts, alkaline earth metal salts or unsubstituted or substituted ammonium salts of higher fatty acids (chains of 10 to 22 carbon atoms), for example the sodium or potassium salts of oleic or stearic acid, or of natural fatty acid mixtures which can be obtained for example from coconut oil or tallow oil. The fatty acid methyltaurin salts may also be used.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammoniums salts and have a 8 to 22 carbon alkyl radical which also includes the alkyl moiety of alkyl radicals, for example, the sodium or calcium salt of lignonsulfonic acid, of dodecylsulfate or of a mixture of fatty alcohol sulfates obtained from natural fatty acids. These compounds also comprise the salts of sulfuric acid esters and sulfonic acids of fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnapthalenesulfonic acid, or of a naphthalenesulfonic acid/formaldehyde condensation product. Also suitable are corresponding phosphates, e.g. salts of the phosphoric acid ester of an adduct of p-nonylphenol with 4 to 14 moles of ethylene oxide.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamine propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants re nonylphenolpolyethoxyethanols, castor oil polyglycol ethers, polypropylene/polyethylene oxide adducts, tributylphenoxypolyethoxyethanol, polyethylene glycol and octylphenoxyethoxyethanol. Fatty acid esters of polyoxyethylene sorbitan and polyoxyethylene sorbitan trioleate are also suitable non-ionic surfactants.

Cationic surfactants are preferably quaternary ammonium salts which have, as N-substituent, at least one $C_8$–$C_{22}$alkyl radical and, as further substituents, lower unsubstituted or halogenated alkyl, benzyl or lower hydroxyalkyl radicals. The salts are preferably in the form of halides, methylsulfates or ethylsulfates, e.g. stearyltrimethylammonium chloride or benzyldi(2-chloroethyl)ethylammonium bromide.

The surfactants customarily employed in the art of formulation are described, for example, in "McCutcheon's Detergents and Emulsifiers Annual," MC Publishing Corp. Ringwood, N.J., 1979, and Sisely and Wood, "Encyclopedia of Surface Active Agents," Chemical Publishing Co., Inc. New York, 1980.

The agrochemical compositions usually contain from about 0.1 to about 99%, preferably about 0.1 to about 95%, and most preferably from about 3 to about 90% of the active ingredient, from about 1 to about 99.9%, preferably from about 1 to about 99%, and most preferably from about 5 to about 95% of a solid or liquid adjuvant, and from about 0 to about 25%, preferably about 0.1 to about 25%, and most preferably from about 0.1 to about 20% of a surfactant.

Whereas commercial products are preferably formulated as concentrates, the end user will normally employ dilute formulations.

The present invention also relates to transgenic plants that contain DNA sequences coding for at least one lytic peptide and at least one hydrolase. Transgenic plants containing DNA sequences coding for chitinase and beta-1,3-glucanase are disclosed in co-pending patent applications Ser. No. 425,504, filed on Oct. 20, 1989 and Ser. No. 381,443, filed on Jul. 18, 1989. The specifications of both of these co-pending applications is hereby expressly incorporated herein.

In transgenic plants, the synthesis of lytic peptides and hydrolytic enzymes may be induced by use of an inducible expression system comprising an inducible gene and an inducing regulator. For example, more than ten of the tobacco PR (pathogen related) protein genes are chemically inducible, Van Loon,; Jamet et al., *Plant Mol. Biol.*, (1986). Three of these genes, PR-2, PR-N and PR-O have been shown to have beta-1,3-glucanase activity, Kauffman et al., *EMBO*, 6: 3209 (1987), and two, PR-P and PR-Q, have been shown to have chitinase activity. Legrand et al., *PNAS USA*, 84: 6750 (1987). Thus, the present invention includes transgenic plants which express a gene encoding at least one lytic peptide followed by treatment with an inducing regulator which induces the accumulation of at least one natural or foreign hydrolytic enzyme.

The invention is illustrated in more detail by the following examples, without implying any restriction to what is described therein.

EXAMPLES

Example 1: Purification of Chitinase and Beta-1,3-glucanase from Ethylene-treated Bean Leaves Step 1: Ethylene treatment and plant material.

Seeds of *Phaseolus vulg. L. cv. saxa* were grown in vermiculite under a 16 hr light: 8 hr dark regime at 20° C. Twelve day old bean plants were incubated in airtight plastic chambers with a volume of 0.2 m$^3$. Control plants were incubated in identical chambers in ethylene-free air. After 48 hours, the primary leaves were harvested and frozen at −20° C.

Step 2: Crude Enzyme Preparation.

0.6597 kg frozen leaf tissue was homogenized in 0.1M sodium citrate buffer at pH 5.0 (2 ml×g$^{-1}$ fresh weight) with a Turmix homogenizer at top speed. The homogenate was centrifuged (25 Min., 11000 g) and 100 ml of the supernatant were used as a crude enzyme preparation. The proteins in the remaining crude extract were precipitated by adding ammonium sulfate to 95% saturation. After centrifugation (30 min., 11000 g) the sediment was redissolved in 100 mM Tris/HCl pH 8.0 and dialyzed against 5 mM Tris/HCl pH 8.0.

Step 3: Enzyme purification.

The dialyzed crude protein fraction was passed through a diethylaminoethyl (DEAE)-trisacryl (IBF, Clichy, F) column equilibrated in 5 mM Tris/HCl pH 8.0. Buffer containing the basic proteins which passed through the column unretarded was brought to a final concentration of 20 mM NaHCO$_3$. The pH was raised to 8.4 with 1M NaOH and the liquid was loaded onto a column of regenerated chitin (Molano et al., *Analyt. Biochem.*, 83:648–656 (1977)) equilibrated in 20 mM $NaHCO_3$. The flow-through was collected and the pH was brought to 5.5 with 1M HCl. The proteins were dialyzed against water and treated three times with a small amount of regenerated chitin, followed by centrifugation to remove traces of chitinase. The fractions containing a high activity of beta-1,3-glucanase were then lyophilized. They are the source of partially purified beta-1,3-glucanase.

The chitin column was washed with 20 mM $NaHCO_3$, followed by 20 mM sodium acetate buffer pH 5.5. Chitinase was eluted with 100 mM acetic acid in an elution volume of 31 ml. The pH of the eluate was brought to 5.5 with 1M KOH and the protein was dialyzed against water and lyophilized. This protein will be the source of purified chitinase.

Step 4: Determination of protein.

Protein was measured as described by Bradford, *Analyt. Biochem.*, 72:248–254 (1976).

Step 5a: Chitinase assay.

Chitinase activity was measured as described by Molano et al. (1977).

Step 5b: Beta-1,3-glucanase assay.

Beta-1,3-glucanase activity was measured as described by Dygert et al., *Analyt. Biochem.*, 13:367–374 (1965).

Step 6: Enzyme induction in ethylene-treated bean leaves.

A 48 hr ethylene treatment led to a strong induction of chitinase and beta-1,3-glucanase, as demonstrated by the results in Table 1:

TABLE I

CHITINASE AND BETA-1,3-GLUCANASE ACTIVITY IN ETHYLENE-TREATED BEAN LEAVES

| | |
|---|---|
| Specific chitinase activity (nkatal/mg protein) | 45.95 |
| Absolute chitinase activity (nkatal/ml extract) | 54.71 |
| Specific beta-1,3-glucanase activity (nkatal/mg protein) | 28.72 |
| Absolute beta-1,3-glucanase activity (nkatal/ml extract) | 34.21 |

Step 7: Enzyme purification.

Table 2 shows the purification protocol of chitinase and beta-1,3-glucanase. Chitinase was 33 times purified with a yield of 21.6%. Beta-1,3-glucanase was purified with a purification factor of 3.0 and a yield of 33.5%. SDS polyacrilamide gel electrophoresis showed that beta-1,3-glucanase is quite highly purified after these purification steps. (Burri (1989)).

Step 8: Induction of chitinase and beta-1,3-glucanase in bean leaves.

In the bean leaves used for this experiment, the enzymes chitinase and beta-1,3-glucanase were slightly less induced than expected. For example, in Burri (1989), the average of five ethylene treatments gave an absolute chitinase activity of 88.86±6.65 nkatal/ml extract and an absolute beta-1,3-glucanase activity of 76.00±6.77 nkatal/ml extract. Therefore, it was decided to define as the unit of standard concentration for chitinase (c=1), the concentration of chitinase necessary to attain an activity of 88.86 nkatal/ml extract. The relative concentration of chitinase extracts were defined in terms of fractions of that activity. The relative concentrations of partially purified beta-1,3-glucanase were defined in terms of fractions of an activity of 76.00 nkatal/ml extract.

Step 9: Chitinase Purification.

Chitinase was purified by affinity chromatography. The purification factor was comparable to that in Burri (1989) (32%).

Step 10: Beta-1,3-glucanase Purification.

The yield of 35.5% is approximately one-third higher than that in Burri (1989) at that purification step while the purification factor of 3.0 is not as high as previously observed.

Example 2: Synthesis of Lytic Peptides.

Lytic peptides are synthesized using an Applied Biosystems Model 430 Peptide Synthesizer according to the manufacturer's recommendations. Peptides are purified by HPLC.

Example 3: The Inhibitory Effect of Lytic Peptides and Hydrolytic Enzymes Against *S. nodorum.*

Test system:

Microtiter plates were selected to investigate the inhibitory effect of lytic peptides and hydrolytic enzymes against *S. nodorum.* Test substances were added to 90 ul liquid pea medium which had been previously inoculated with $2.0\times10^4$ spores/ml medium of the test pathogen to give a final volume of 100 ul. The blank value of the test substances were determined by adding them to uninoculated liquid pea medium. The plates were evaluated after incubation in a wet chamber at 23° C. on a shaker in the dark for 48 hours.

Test solutions:

a. Hydrolytic enzymes were purified from ethylene-treated bean leaves by the procedure described in Example 1.

b. Lytic peptides: The following antimicrobial peptides were tested at 20 ppm, 60 ppm and 200 ppm concentrations:

TABLE 2

Purification protocol of chitinase and β-1,3-glucanase from ethylene-treated bean leaves

| | Total protein (mg) | Total chitinase activity (nkatal) [yield] | Specific chitinase activity (nkatal/mg protein) | Total β-1,3-glucanase activity (nkatal) [yield] | Specific β-1,3-glucanase activity (nkatal/mg protein) |
|---|---|---|---|---|---|
| Crude extract | 740 | 34001<br>100% | 45.95 | 22566<br>100% | 28.7 |
| Redissolved ammonium sulfate precipitate | 524 | 31944<br>94% | 60.94 | not measured | not measured |
| DEAE-column flow through | 191.4 | 26598<br>78.20% | 139 | 8991<br>42.30% | 52.6 |
| Purified chitinase | 4.84 | 7341<br>21.60% | 1517 | 11.78 | 2.43 |
| Chitin-column flow through | 82.1 | 701 | 8.54 | 7129<br>33.50% | 86.6 |

Synthetic peptide No. 3
Mellitin c. Controls:
Water control: 10 ul distilled water were added to 90 ul spore solution.

d. Combinations of test substances: Table 3 illustrates the composition of test solutions which were tested in duplicate/triplicate samples.

e. Evaluation: The growth of the pathogen was recorded by measuring the absorbance of the medium at 595 nm. The average of duplicate/triplicate samples was calculated and the corresponding enzyme blank was subtracted to give the net absorption of the growing mycelium. The inhibitory effect of the test substances used was determined by calculating the growth of the pathogen as a percentage of water control.

f. Results: The results of the above described test are compiled in Table 4. When applied as single test solutions, all test substances were able to inhibit growth of S. nodorum to a limited extent, depending upon the concentrations used. The combination of partially purified beta-1,3-glucanase and lytic peptide was found to inhibit pathogenic growth more strongly than combinations of purified chitinase and lytic peptide. This is consistent with the finding that S. nodorum was more sensitive to partially purified beta-1,3-glucanase than to purified chitinase. As Table 3 demonstrates, additions of 1/100 c of either enzyme to a particular lytic peptide concentration only slightly increases the inhibitory effect of the test substance in comparison with the lytic peptide alone. Combinations of 1/10 c of either enzyme with a particular lytic peptide concentration more strongly inhibit the test pathogen than combinations of 1/100 c enzyme with lytic peptide. It is especially interesting that combinations of both enzymes, either in 1/10 c or 1/100 c concentration, with lytic peptides strongly increase the inhibitory effect of the test substances.

TABLE 3

| | TEST SOLUTIONS | | |
|---|---|---|---|
| Sample | Purified Chitinase (c) | Purified Beta-1,3-Glucanase (c) | Lytic Peptide (ppm) |
| 0 | — | — | — |
| 1 | 1/10 | — | — |
| 2 | 1/100 | — | — |
| 3 | — | 1/10 | — |
| 4 | — | 1/100 | — |
| 5 | — | — | 20 |
| 6 | — | — | 60 |
| 7 | — | — | 200 |
| 8 | 1/10 | 1/10 | — |
| 9 | 1/10 | 1/100 | — |
| 10 | 1/100 | 1/10 | — |
| 11 | 1/100 | 1/100 | — |
| 12 | 1/10 | — | 20 |
| 13 | 1/10 | — | 60 |
| 14 | 1/10 | — | 200 |
| 15 | 1/100 | — | 20 |
| 16 | 1/100 | — | 60 |
| 17 | 1/100 | — | 200 |
| 18 | — | 1/10 | 20 |
| 19 | — | 1/10 | 60 |
| 20 | — | 1/10 | 200 |
| 21 | — | 1/100 | 20 |
| 22 | — | 1/100 | 60 |
| 23 | — | 1/100 | 200 |
| 24 | 1/10 | 1/10 | 20 |
| 25 | 1/10 | 1/10 | 60 |
| 26 | 1/10 | 1/10 | 200 |
| 27 | 1/100 | 1/100 | 20 |
| 28 | 1/100 | 1/100 | 60 |
| 29 | 1/100 | 1/100 | 200 |

TABLE 4

RESULTS OF TEST SOLUTIONS
FUNGAL GROWTH IN PERCENTAGE OF CONTROL

| TEST SOLUTION | SYNTHETIC PEPTIDE NO. 3 | MELLITIN | ENZYMES |
|---|---|---|---|
| 0 (Control) | — | — | 100.00 |
| 1 | — | — | 78.60 |
| 2 | — | — | 93.68 |
| 3 | — | — | 50.18 |
| 4 | — | — | 81.75 |
| 5 | 80.35 | 79.65 | — |
| 6 | 73.51 | 65.96 | — |
| 7 | 65.96 | 27.37 | — |
| 8 | — | — | 34.21 |
| 9 | — | — | 45.61 |
| 10 | — | — | 39.82 |
| 11 | — | — | 60.88 |
| 12 | 68.42 | 62.81 | — |
| 13 | 63.51 | 57.54 | — |
| 14 | 61.75 | 22.46 | — |
| 15 | 77.89 | 73.33 | — |
| 16 | 71.58 | 65.26 | — |
| 17 | 64.21 | 25.61 | — |
| 18 | 46.67 | 14.74 | — |
| 19 | 30.88 | 11.93 | — |
| 20 | 27.89 | 6.32 | — |
| 21 | 65.26 | 61.40 | — |
| 22 | 63.51 | 57.19 | — |
| 23 | 53.68 | 25.96 | — |
| 24 | 9.47 | 10.53 | — |
| 25 | 8.42 | 7.37 | — |
| 26 | 3.86 | 0.00 | — |
| 27 | 40.7 | 22.72 | — |
| 28 | 36.49 | 22.11 | — |
| 29 | 31.23 | 18.75 | — |

Example 4: Formulations of Anti-Pathogenically Effective Compositions Employing Liquid Compositions of Lytic Peptides and Hydrolytic Enzymes as the Active Ingredient.

In the following examples, percentages of composition are given by weight:

| 1. Emulsifiable concentrates: | a | b | c |
|---|---|---|---|
| Active ingredient | 20% | 40% | 50% |
| Calcium dodecylbenzenesulfonate | 5% | 8% | 6% |
| Castor oil polyethlene glycol ether (36 moles of ethylene oxide) | 5% | — | — |
| Tributylphenol polyethylene glycol ether (30 moles of ethylene oxide) | — | 12% | 4% |
| Cyclohexanone | — | 15% | 20% |
| Xylene mixture | 70% | 25% | 20% |

Emulsions of any required concentration can be produced from such concentrates by dilution with water.

| 2. Solutions: | a | b | c | d |
|---|---|---|---|---|
| Active ingredient | 80% | 10% | 5% | 95% |
| Ethylene glycol monomethyl ether | 20% | — | — | — |
| Polyethylene glycol 400 | — | 70% | — | — |
| N-methyl-2-pyrrolidone | — | 20% | — | — |
| Epoxidised coconut oil | — | — | 1% | 5% |
| Petroleum distillate (boiling range 160–190°) | — | — | 94% | — |

These solutions are suitable for application in the form of microdrops.

| 3. Granulates: | a | b |
|---|---|---|
| Active ingredient | 5% | 10% |

-continued

| 3. Granulates: | a | b |
|---|---|---|
| Kaolin | 94% | — |
| Highly dispersed silicic acid | 1% | — |
| Attapulgite | — | 90% |

The active ingredient is dissolved in methylene chloride, the solution is sprayed onto the carrier, and the solvent is subsequently evaporated off in vacuo.

| 4. Dusts: | a | b |
|---|---|---|
| Active ingredient | 2% | 5% |
| Highly dispersed silicic acid | 1% | 5% |
| Talcum | 97% | — |
| Kaolin | — | 90% |

Ready-to-use dusts are obtained by intimately mixing the carriers with the active ingredient.

Example 5: Formulation of Anti-Pathogenically Effective Compositions Employing Solid Compositions of Lytic Peptides and Hydrolytic Enzymes as the Active Ingredient.

In the following examples, percentages of compositions are by weight.

| 1. Wettable powders: | a | b | c |
|---|---|---|---|
| Active ingredient | 20% | 60% | 75% |
| Sodium lignosulfonate | 5% | 5% | — |
| Sodium lauryl sulfate | 3% | — | 5% |
| Sodium diisobutylnaphthalene-sulfonate | — | 6% | 10% |
| Octylphenol polyethylene glycol ether (7–8 moles of ethylene oxide) | — | 2% | — |
| Highly dispersed silicic acid | 5% | 27% | 10% |
| Kaolin | 67% | — | — |

The active ingredient is thoroughly mixed with the adjuvants and the mixture is thoroughly ground in a suitable mill, affording wettable powders which can be diluted with water to give suspensions of the desired concentrations.

| 2. Emulsifiable concentrate: | |
|---|---|
| Active ingredient | 10% |
| Octylphenol polyethylene glycol ether (4–5 moles of ethylene oxide) | 3% |
| Calcium dodecylbenzenesulfonate | 3% |
| Castor oil polyglycol ether (36 moles of ethylene oxide) | 4% |
| Cyclohexanone | 30% |
| Xylene mixture | 50% |

Emulsions of any required concentration can be obtained from this concentrate by dilution with water.

| 3. Dusts: | a | b |
|---|---|---|
| Active ingredient | 5% | 8% |
| Talcum | 95% | — |
| Kaolin | — | 92% |

Ready-to-use dusts are obtained by mixing the active ingredient with the carriers, and grinding the mixture in a suitable mill.

| 4. Extruder granulate: | |
|---|---|
| Active ingredient | 10% |
| Sodium lignosulfonate | 2% |
| Carboxymethylcellulose | 1% |
| Kaolin | 87% |

The active ingredient is mixed and ground with the adjuvants, and the mixture is subsequently moistened with water. The mixture is extruded and then dried in a stream of air.

| 5. Coated granulate: | |
|---|---|
| Active ingredient | 3% |
| Polyethylene glycol 200 | 3% |
| Kaolin | 94% |

The finely ground active ingredient is uniformly applied, in a mixer, to the kaolin moistened with polyethylene glycol. Non-dusty coated granulates are obtained in this manner.

| 6. Suspension concentrate: | |
|---|---|
| Active ingredient | 40% |
| Ethylene glycol | 10% |
| Nonylphenol polyethylene glycol (15 moles of ethylene oxide) | 6% |
| Sodium lignosulfonate | 10% |
| Carboxymethylcellulose | 1% |
| 37% aqueous formaldehyde solution | 0.2% |
| Silicone oil in 75% aqueous emulsion | 0.8% |
| Water | 32% |

The finely ground active ingredient is intimately mixed with the adjuvants, giving a suspension concentrate from which suspensions of any desire concentration can be obtained by dilution with water.

Example 6: Stable Transformation and Regeneration of Transgenic Plants.

The construction of plasmid pCIB1005B, which contains a double 35S cauliflower mosaic virus (CaMV) promoter operably linked to a gene encoding for the expression of basic glucanase, and of pGN1781C, a binary vector containing a functional fragment of pCIB1005B, is described in co-pending patent application Ser. No. 425,504, filed on Oct. 20, 1989. The specification of that application is hereby incorporated by reference.

The construction of plasmid pCIB1007, which contains a double 35S CaMV promoter operably linked to a gene encoding for the expression of basic chitinase, and of pGN1782C, a binary vector containing a functional fragment of pCIB1007, is described in co-pending patent application Ser. No. 425,504, filed on Oct. 20, 1989.

Example 7: Construction of a Synthetic Gene Encoding Synthetic Lytic Peptide No. 3.

The synthetic lytic peptide No. 3 as described in the above examples has the following amino acid sequence:

GIGKFLHSAK KFGFAFVGIM NS.

A synthetic gene encoding this peptide is constructed in several steps. First a gene encoding the mature (processed) protein is synthesized and cloned, then a signal peptide and 5' leader sequence for expression in plants and secretion are added, finally a 3' untranslated sequence and 3' mRNA processing site are added. This results in a gene encoding synthetic peptide No. 3 which can be transformed into a plant and which will direct the synthesis of a lytic peptide which will be secreted extracellularly.

A. Construction of the Coding Sequence for the Mature Peptide.

Two oligonucleotides are synthesized, Oligo 1 and Oligo 2, with the following sequence:

OLIGO 1: 5' GAATTCGGGA TCGGCAAGTT CCTGCACAGC GCCAAGAAGT TCGGGAAGGC CTTCGTGGGC ATCATGAACA GCTAA 3'

OLIGO 2: 5' GAATTCTTAG CTGTTCATGA TGCCCACGAA GGCCTTCCCG AACTTCTTGG CGCTGTGCAG GAACTTGCCG ATCCC 3'

The oligonucleotides are synthesized using beta-cyanoethyl-phosphoramidite chemistry on an Applied Biosystems 380A synthesizer and are purified using OPC-based purification (Applied Biosystems) as described by the supplier. The purified oligonucleotides are first kinased with polynucleotide kinase and then annealed for one hour at 65° C. The reaction is cooled to 37° C. and T4 DNA ligase added along with extra ATP and the ligation is allowed to incubate a further hour. The reaction is then heated to 65° C. for 15 minutes to inactivate the ligase and then diluted and made 1× in the recommended EcoRI buffer. The ligation reaction is then digested with EcoRI. The DNA is phenol extracted and precipitated with 0.3M sodium acetate and two volumes of ethanol. The precipitate is collected by centrifugation and resuspended in 10 mM TE buffer (Maniatis new volume). The DNA is electrophoresed on a 3.0% low gelling temperature agarose gel and the band containing the synthetic gene is excised and ligated into the EcoRI site of pBluescript (Stratagene). The ligation reaction is transformed into *E. coli* and colonies are selected and putative positive constructs are analyzed first by restriction digestion and then by DNA sequencing. One construct which is designated pBSlypep3 is determined to contain the correct sequence and is chosen for further work.

B. Addition of a 5' Flanking Sequence and Signal Peptide to pBSlypep3.

The 5' leader and signal peptide of the PR-1a gene are added to the syntheic gene using a PCR based in vitro gene fusion technique as described by Ho et al., *Gene*, 77:51–59 (1989). In this technique a gene fusion is made in vitro by creating two fragments with overlapping ends by PCR. In a subsequent reaction these two fragments are then fused, again by PCR, to generate a perfect fusion between the two molecules. This strategy is used to fuse the PR-1a signal peptide and leader to the coding sequence for the lytic peptide. To accomplish this fusion four oligonucleotides are synthesized and purified as described above:

Oligo 3: 5' TATCCCACTCTTGCCGTGCCC-GGATCGGCAAGTTCCTG 3'

Oligo 4: 5' CAGGAACTTGCCGATCCCGGCACG-GCAAGAGTGGGATA 3'

Oligo 5: 5' GATCGAATTCATT-CAAGATACAACATTTCT 3'

Oligo 6: 5' GAATTCTTAGCTGTTCATGATGC-CCAC 3'

The oligos 3 and 4 are complementary to each other and contain the DNA sequence desired for the fusion between the PR-1a signal and leader and the lytic peptide coding sequence. The desired fusion is diagrammed below:

Oligo 3: 5' TATCCCACTCTTGCCGTGCCGGGATCGGCAAGTTCCTG 3'
3' ATAGGGTGAGAACGGCACGGCCCTAGCCGTTCAAGGAC 5': Oligo 4
| PR-1a | | lytic peptide 3 |

The oligo 5 has the same sequence as the 5' end of the PR-1a cDNA and it contains on the 5' end a sequence encoding an EcoRI restriction site.

Oligo 5: 5' GATCGAATTCATTCAAGATACAACATTTCT 3'
| EcoRI | PR-1a |

The oligo 6 is complementary to the 3' end of the synthetic gene encoding lytic peptide 3 and also contains an EcoRI site at the 5' end:

Oligo 6: 5' GAATTCTTAGCTGTTCATGATGC-CCAC 3'

In order to fuse the two pieces of DNA, two PCR reactions are set up. One which uses Oligo 3 and Oligo 6 as primers and the plasmid pBSLypep3 as a template and the other which uses Oligo 4 and Oligo 5 as primers and the plasmid pBS-PR1013Cla (ATCC #67628, deposited Feb. 11, 1988) as a template. The PCR reactions are carried out using the GeneAmp kit (Perkin Elmer/CETUS) as suggested by the suppliers. The PCR products are analyzed by agarose gel electrophoresis and it is determined that the reaction is successful. The PCR products are then purified and an aliquot of each is used in a second stage PCR reaction. In this reaction the primers, Oligo 5 and Oligo 6, are used to amplify the product. In this way the two pieces of DNA are fused in the predetermined manner explained above. The reaction products are analyzed by agarose gel electrophoresis and it is determined that the reaction is successful. The DNA is then phenol extracted and ethanol precipitated and the DNA resuspended and digested with EcoRI. This DNA is then purified by electrophoresis on a low-gelling temperature agarose gel and ligated into pbluescript which is digested with EcoRI and treated with CIAP. The DNA is transformed into *E. coli* and transformants are selected. Positive plasmid constructs are screened by restriction digestion and confirmed for the anticipated structure by DNA sequencing. One such construct is designated pBSLP5'PR1 and is used for subsequent experiments.

C. Subcloning the Lytic Peptide Gene into a Double 35S Expression Vector.

The synthetic lytic peptide gene with a 5' leader sequence and a signal peptide is subcloned into the plant expression vector, pCGN1761, which is a vector that supplies a double CAMV 35S promoter and a 3' mRNA processing site. The construction of the pCGN1761 vector has been described in the co-pending patent application, Ser. No. 425,504, which was filed on Oct. 20, 1989.

The plasmid pBSLP5'PR1 is digested with EcoRI and the approximately 200 bp fragment containing the lytic peptide gene and PR-1a signal/leader is purified from a low-gelling temperature agarose gel. This fragment is ligated into pCGN1761 which is digested with EcoRI and treated with CIAP and also purified on low-gelling temperature agarose. The ligation reaction is used to transform E. coli and transformants are selected and then screened for the insert. Two types of transformants are recovered which differ in the orientation of the lytic peptide gene. One type, in which the gene is in the "sense" orientation with respect to the promoter, is selected and several plasmids are verified for the correct construct by DNA sequencing. One plasmid, which has the correct orientation and the anticipated DNA sequence, is designated pBS2X35SLytPep and used in further experiments.

D. Subcloning the 2X35S CAMV/lytic Peptide Expression Cassette into a Binary Vector.

The expression cassette is subcloned into the pCGN1540 binary vector. The construction of this vector is described in the co-pending patent application, Ser. No. 425,504, filed on Oct. 20, 1989. The vector has been deposited into the ATCC, accession number 40586, accession date Mar. 24, 1989.

The XbaI fragment of pBS2X35SLytPep, which contains the lytic peptide gene, is subcloned into the XbaI site of pCGN1540 in such a way that the promoter fragment is proximal to the plant selectable marker gene. This plasmid is designated pBSBin2X35SLytPep and is selected for further experiments.

E. Transformation of Agrobacterium.

The transformation of Agrobacterium tumafaciens with binary vectors has been described in the co-pending patent application, Ser. No. 425,504, filed on Oct. 20, 1989. The plasmid pBSBin2X35SLytPep is transformed into Agrobacterium and positive colonies are selected and verified by Southern blot analysis and used for plant transformation experiments.

Plant tissue is transformed with the vectors described above by any technique known in the art. The stable transformation of plants and regeneration of transgenic plants is described in co-pending patent application, Ser. No. 305,566, filed on Feb. 6, 1989, the specification of which is hereby incorporated by reference.

To obtain plants containing all three genes, homozygous T3 plants are made as described in co-pending patent application, Ser. No. 425,504, filed on Oct. 20, 1989. Conventional breeding techniques are then used to get all three genes into the same plant.

While the present invention has been described with reference to specific embodiments thereof, it will be appreciated that numerous variations, modifications, and embodiments are possible, and accordingly, all such variations, modifications and embodiments are to be regarded as being within the spirit and scope of the present invention.

What is claimed is:

1. A composition for controlling plant pathogens, comprising an antipathogenically effective amount of an active ingredient and one or more agriculturally acceptable carriers, wherein said active ingredient comprises a) a lytic peptide which is a mellitin or a magainin; b) a chitinase; and c) a beta-1,3-glucanase.

2. A composition of claim 1 wherein said chitinase is present in said active ingredient at a relative concentration of about 1/10 c.

3. A composition of claim 1 wherein said chitinase is present in said active ingredient at a relative concentration of about 1/100 c.

4. A composition of claim 1 wherein said beta-1,3-glucanase is present in said active ingredient at a relative concentration of about 1/10 c.

5. A composition of claim 1 wherein said beta-1,3-glucanase is present in said active ingredient at a relative concentration of about 1/100 c.

6. A composition of claim 1 wherein said chitinase is present in said active ingredient at a relative concentration of about 1/10 c and said beta-1,3-glucanase is present in said active ingredient at a relative concentration of about 1/10 c.

7. A composition of claim 1 wherein said chitinase is present in said active ingredient at a relative concentration of about 1/10 c and said beta-1,3-glucanase is present in said active ingredient at a relative concentration of about 1/100 c.

8. A composition of claim 1 wherein said chitinase is present in said active ingredient at a relative concentration of about 1/100 c and said beta-1,3-glucanase is present in said active ingredient at a relative concentration of about 1/100 c.

9. A composition of claim 1 wherein said chitinase is present in said active ingredient at a relative concentration of about 1/100 c and said beta-1,3-glucanase is present in said active ingredient at a relative concentration of about 1/10 c.

10. A composition of claim 1 wherein the lytic peptide is the magainin designated as synthetic peptide no. 3.

11. A composition of claim 1 wherein the lytic peptide is mellitin.

12. A composition of claim 1, wherein the lytic peptide is present in a concentration from about 20 ppm to about 200 ppm.

* * * * *